United States Patent [19]

Ikeda et al.

[11] Patent Number: 5,939,552
[45] Date of Patent: Aug. 17, 1999

[54] PROCESS FOR PREPARING OPTICALLY ACTIVE MEVALONOLACTONE COMPOUNDS

[75] Inventors: Hirokazu Ikeda; Tatsushi Murakami, both of Hyogo-ken; Hiroo Matsumoto, Chiba-ken; Yoshio Ohara, Chiba-ken; Hiroyasu Kanda, Chiba-ken, all of Japan

[73] Assignees: Daicel Chemical Industries, Ltd., Osaka-fu; Nissan Chemical Industries, Ltd., Tokyo, both of Japan

[21] Appl. No.: 08/700,396

[22] PCT Filed: Feb. 22, 1995

[86] PCT No.: PCT/JP95/00251

§ 371 Date: Aug. 22, 1996

§ 102(e) Date: Aug. 22, 1996

[87] PCT Pub. No.: WO95/23125

PCT Pub. Date: Aug. 31, 1995

[30] Foreign Application Priority Data

Feb. 25, 1994 [JP] Japan .................................. 6-028594

[51] Int. Cl.$^6$ .................................................. C07D 215/00
[52] U.S. Cl. ........................................... 546/152; 546/174
[58] Field of Search ...................................... 546/152, 174

[56] References Cited

U.S. PATENT DOCUMENTS 5,284,953   2/1994   Ohara et al. ............................. 546/173

FOREIGN PATENT DOCUMENTS

| 131761 | 5/1992 | Japan . |
|---|---|---|
| 4-131761 | 5/1992 | Japan . |
| 5-148237 | 6/1993 | Japan . |

*Primary Examiner*—Amelia Owens
*Attorney, Agent, or Firm*—Birch, Stewart, Kolasch & Birch, LLP

[57] ABSTRACT

The process for preparing mevalonolactone compounds is carried out by means of batch system chromatography or a simulated moving bed chromatographic process using columns filled with an optical resolution filler comprising a polysaccharide derivative. The simulated moving bed chromatographic process comprises forming a circulation flow circuit comprising a plurality of columns endlessly connected in series; enforcing a fluid to flow through the circuit in one direction; providing the column series alternately with an inlet port through which the fluid is introduced into the column in the flow direction and with an outlet port, through which the fluid is taken out; intermittently shifting activation of the inlet port and the outlet port in the direction of the fluid flow; introducing a solution containing a racemic mevalonolactone compound and an eluent through an inlet port into the circuit; and simultaneously taking out a solution rich in the weakly adsorbable substance and a solution rich in the strongly adsorbable and desorbed substance through the outlet port.

5 Claims, 2 Drawing Sheets

PROCESS FOR PREPARING OPTICALLY ACTIVE MEVALONOLACTONE COMPOUNDS

TECHNICAL FIELD THE INVENTION

This invention relates to a process for preparing optically active mevalonolactone compounds. More particularly, this invention relates to a commercial process for preparing optically active mevalonolactone compounds which are useful for prevention and treatment of hyperlipemia, arteriosclerosis, etc.

BACKGROUND OF THE INVENTION

With respect to pharmaceutical compounds which have an asymmetric center, it is known that optical isomers of some of such compounds respectively have different physiological activities. That is, often only one of the isomers has physiological effect in vivo or only one of them has teratogeneticity as seen in thalidomide. However, it is difficult to optically separate a racemic compound by a conventional method such as distillation, crystallization, etc. Thus most of the pharmaceutical compounds having an asymmetric center are marketed in the form of a racemic compound.

Under the circumstances, a commercial process, by which only an optical isomer of various such pharmaceutical compounds and intermediate compounds therefor can be isolated, is strongly desired. Because, if only physiologically active and useful isomers can be used as therapeutics, a small dose suffices and abatement of undesirable side effect is expected.

Although physiologically active isomers of mevalonolactone compounds are very useful for prevention and treatment of hyperlipemia, arteriosclerosis, etc., there has been no commercial process for optical resolution.

The object of this invention is to solve the above-described problem. In other words, the object of this invention is to isolate optically active isomers of mevalonolactone compounds with high purity in a commercial scale.

DISCLOSURE OF THE INVENTION

In the present invention, batch system chromatography and simulated moving bed chromatographic process using columns filled with a filler for optical resolution are employed in order to solve the above-described problem.

More particularly, the invention described in claim 1 is a process for preparing an optically active mevalonolactone compound comprising conducting optical resolution of the racemic mixture of an optically active mevalonolactone compound by means of batch system chromatography which uses a column filled with a filler selected from a group consisting of particles of a polysaccharide ester derivative, particles of a polysaccharide carbamate derivative and particles of a support which carries a polysaccharide ester derivative and/or a polysaccharide carbamate derivative.

The invention described in claim 2 is a process for preparing an optically active mevalonolactone compound as described in claim 1, wherein the polysaccharide ester derivative and the polysaccharide carbamate derivative are those in which part of or all of the hydrogen atoms on the hydroxy groups or amino groups of the polysaccharide are substituted with an atom groups represented by any of the following chemical formulas (1) to (4):

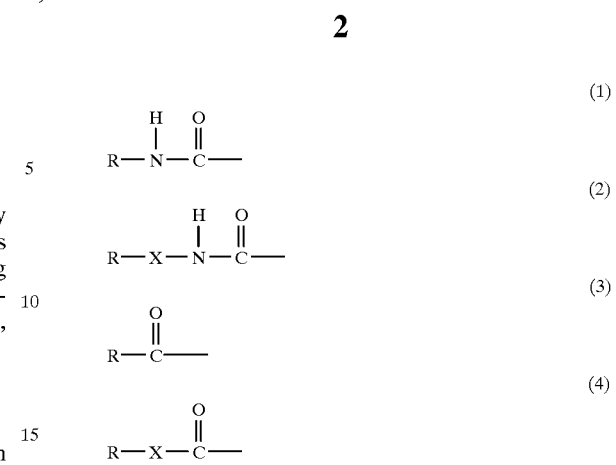

wherein R stands for an aromatic group which may contain a hetero atom and may be unsubstituted or substituted with at least one selected from a group consisting of an alkyl group having 1–12 carbon atoms, an alkoxy group having 1–12 carbon atoms, an alkylthio group having 1–12 carbon atoms, a cyano group, a halogen atom, an acyl group having 1–8 carbon atoms, an acyloxy group having 1–8 carbon atoms, a hydroxy group, an alkoxycarbonyl group having 1–12 carbon atoms, a nitro group, an amino group and an alkylamino group having 1–8 carbon atoms; and X stands for a hydrocarbon group having 1–4 carbon atoms, which may contain a double bond or triple bond.

The invention described in claim 3 is a process for preparing an optically active mevalonolactone compound comprising forming a circulation flow circuit comprising a plurality of columns filled with an optical resolution filler and endlessly connected in series; enforcing a fluid to flow through the circuit in one direction; providing each with an inlet port through which the fluid is introduced into the column in the flow direction and with an outlet port, through which the fluid is taken out; intermittently shifting the working position of the inlet port and a suitably-spaced outlet port in the direction of the fluid flow; introducing a solution containing a racemic mevalonolacton compound and an eluent through an inlet port into the circuit; and simultaneously taking out a solution rich in the weakly adsorbable and a solution rich in the strongly adsorbable through the outlet port.

The invention described in claim 4 is a process for preparing an optically active mevalonolactone compound as described in claim 3, wherein the optical resolution filler is one selected from a group consisting of particles of a polysaccharide ester derivative, particles of a polysaccharide carbamate derivative and particles of a support which carries a polysaccharide ester derivative and/or a polysaccharide carbamate derivative.

The invention described in claim 5 is a process for preparing an optically active mevalonolacton compound as described in claim 4, wherein the polysaccharide ester derivative and the polysaccharide are those in which part of or all of the hydrogen atoms on the hydroxy groups or amino groups of the polysaccharide are substituted with any of the atom groups represented by the following chemical formulas (1) to (4):

(2)

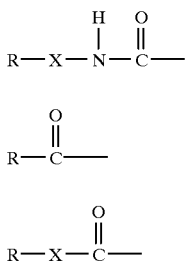

(3)

$$R-\overset{O}{\underset{\|}{C}}-$$

(4)

$$R-X-\overset{O}{\underset{\|}{C}}-$$

wherein R stands for an aromatic group which may contain a hetero atom and may be unsubstituted or substituted with at least one selected from a group consisting of an alkyl group having 1–12 carbon atoms, an alkoxy group having 1–12 carbon atoms, an alkylthio group having 1–12 carbon atoms, a cyano group, a halogen atom, an acyl group having 1–8 carbon atoms, an acyloxy group having 1–8 carbon atoms, a hydroxy group, an alkoxycarbonyl group having 1–12 carbon atoms, a nitro group, an amino group and an alkylamino group having 1–8 carbon atoms; and X stands for a hydrocarbon group having 1–4 carbon atoms, which may contain a double bond or triple bond.

The invention described in claim 6 is a process for preparing an optically active mevalonolactone compound as described in any of claims 1 to 5, wherein the optically active mevalonolactone compound is ethyl 7-[2-cyclopropyl-4-(4-fluorophenyl)quinolin-3-yl]-5-hydroxy-3-oxo-6-heptenoate or ethyl 7-[2-cyclopropyl-4-(4-fluorophenyl)quinolin-3-yl]-3,5-dihydroxy-6-heptenoate.

Mevalonolactone compounds handled in the process of the present invention are represented by a chemical formula (5)

(5)

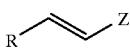

wherein R is a carbocyclic aromatic group, heterocyclic aromatic group or fused ring heterocyclic aromatic groups having a sp² carbon atom; and Z is a group represented by a chemical formula (6):

(6)

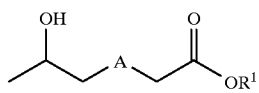

wherein A stands for

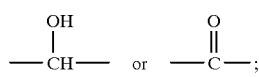

$R^1$ is a hydrogen atom, a straight chain or branched $C_{1-4}$ alkyl, phenyl or aralkyl; or Z is a group represented by a chemical formula (7):

(7)

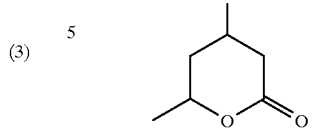

Specific examples of the mevalonolactone compounds represented by chemical formula (5) are ethyl 7-[2-cyclopropyl-4(4-fluorophenyl)quinolin-3-yl]-5-hydroxy-3-oxo-6-heptenoate represented by formula (8), ethyl 7-[2-cyclopropyl-4(4-fluorophenyl)quinolin-3-yl]-3,5-hydroxy-6-heptenoate represented by formula (9) and 6-[2-{2-cyclopropyl-4-(4-fluorophenyl)-quinolin-3-yl}ethenyl]-4-hydroxy-3,4,5,6-tetrahydro-2H-pyran-2-on represented by formula (10)

(8)

(9)

(10)

Now we will discuss the optical resolution fillers used in the present invention.

Various resolution fillers can be used without any limitation if they are able to optically separate a racemic mixture of optically active mevalonolactone compounds. Preferred optical resolution fillers usable in the present invention are selected from a group consisting of particles of a polysaccharide ester derivative, particles of a polysaccharide carbamate derivative and particles on which a polysaccharide ester derivative and/or a polysaccharide carbamate derivative is supported.

The polysaccharide of the above-mentioned polysaccharide ester derivative and polysaccharide carbamate derivative can be any of naturally occurring polysaccharide, modified natural polysaccharide, synthesized polysaccharide as well as oligo sugars. They can be used without any limitation insofar as they are optically active.

Specific examples of the polysaccharides are: α-1,4-glucane (starch, glycogen, amylose), β-1,4-glucan (cellulose), α-1,6-glucan (dextran), β-1,3-glucan (curdlan, schizophylan), α-1,3-glucan, β-1,2-glucan (Crawn Gall polysaccharide) α-1,6-mannan, β-1,4-mannan, β-1,2-fructan (inuline), β-2,6-fructan (levan), β-1,4-xylan, β-1,3-xylan, β-1,4-chitosan, β-1,4-N-acetylchitosan (chitin), α-1,3-1,6-glucan (mutan), pullulan, agalose, arginic acid, etc.

The number average polymerization degree (an average number of pyranose or furanose rings) of these polysaccharides is up to 2,000. However, it is preferably not more than 500 in view of ease in handling.

As oligo sugars, maltose, maltotetraose, maltopentose, maltohexose, maltoheptose, isomaltose, eruose, paratinose, maltitol, maltotriisotol, maltotetraitol, isomaltitol, α-cyclodextrin, β-cyclodextrin, gamma-cyclodextrin, etc. can be referred to.

Examples of preferred polysaccharide ester derivatives and polysaccharide carbamate derivative are polysaccharide compounds, of which part of or all of the hydrogen atoms of the hydroxy or amino groups is substituted with at least one of atom groups represented by the chemical formulas (1), (2), (3) and (4):

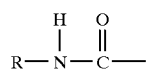

(1)

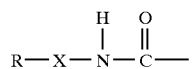

(2)

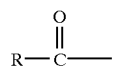

(3)

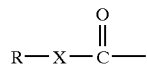

(4)

wherein R stands for an aromatic group which may contain a hetero atom and may be unsubstituted or substituted with at least one selected from a group consisting of an alkyl group having 1–12 carbon atoms, an alkoxy group having 1–12 carbon atoms, an alkylthio group having 1–12 carbon atoms, a cyano group, a halogen atom, an acyl group having 1–8 carbon atoms, an acyloxy group having 1–8 carbon atoms, a hydroxy group, an alkoxycarbonyl group having 1–12 carbon atoms, a nitro group, an amino group and an alkylamino group having 1–8 carbon atoms.

Examples of the aromatic groups are phenyl, naphthyl, phenanthryl, antracyl, indenyl, indanyl, furyl, thionyl, pyryl, benzofuryl, benzothionyl, indyl, pyridyl, pyrimidyl, quinolyl, isoquinolyl, etc. of these, phenyl, naphthyl, pyridyl, etc. are preferred.

X stands for a hydrocarbon group having 1–4 carbon atoms, which may contain a double bond or triple bond.

Examples of X are methylene, ethylene, ethylidene, ethenylene, ethynylene, 1,2- or 1,3-propylene, 1,1- or 2,2-propylidine group, etc.

The degree of substitution with these atom groups is not less than 30%, preferably not less than 50% and more preferably not less than 80%.

The polysaccharides having the above substituents can be prepared by reacting an acid chloride or an isocyanate with the hydroxy or amino groups of a polysaccharide.

In the process of this invention, particles of the above-mentioned polysaccharide ester derivatives and/or polysaccharide carbamate derivatives can be used as optical resolution fillers. In this case, the particle size of the polysaccharide ester derivatives and the polysaccharide carbamate derivatives is usually 1 μm–1 mm, preferably 5 μm–300 μm. The particles of polysaccharide ester derivatives and polysaccharide carbamate derivatives may be poreless but it is preferred that they are porous. The pore diameter of the porous particles is 10 Å–100 μm, preferably 10 Å–5,000 Å.

In the process of the present invention, particles on which the above-described polysaccharide ester derivatives and/or polysaccharide carbamate derivatives are supported, can be used as an optical resolution filler.

Organic and inorganic substances which can support the above-mentioned polysaccharide ester derivatives or polysaccharide carbamate derivatives can be used as supports. Examples of the organic supports are particles of polymers such as polystyrene, polyacrylamide, polyacrylate, etc. Examples of inorganic supports are silica gel, alumina, magnesia, zirconia, glass, kaolin, titanium oxide, silicate salts, diatomaceous earth, etc. The supports may be treated for modification of surface properties.

These supports usually have a particle size of 1 μm–1 mm, preferably 5 μm–300 μm. The particles may be poreless although it is preferred that they are porous. When they are porous, the pore size is 10 Å–100 μm, preferably 100 Å–5,000 Å. μm. The amount of the above-described polysaccharide ester derivatives and/or polysaccharide carbamate derivatives is usually 1–100 wt % of the amount of the support, preferably 5–50 wt %. With not more than 1 wt %, optical resolution of a mevalonolactone may not be satisfactorily effected. If the amount is in excess of 100 wt %, corresponding effect may not be expected.

In the process of this invention, as organic solvents, alcohols such as methanol, ethanol, propanol, etc., hydrocarbons such as hexane as well as a mixed solvent such as a mixture of a hydrocarbon and an alcohol, can be used as eluent for both batch system chromatography and simulated moving bed chromatographic process. A preferred eluent can be suitably selected depending upon the species of the mevalonolactone compound subjected to optical resolution.

The batch system chromatography employed in the present invention is known per se and commonly used.

The simulated moving bed chromatographic process comprises forming a flow circuit by endlessly connecting in series a plurality of columns filled with an optical resolution filler; enforcing a fluid to circulate through the circuit in one direction; providing the columns with an inlet port through which the fluid is introduced into the circuit in the direction of the fluid flow and an outlet port through which the liquid is taken out; shifting the working positions of the inlet port and a suitably spaced outlet port intermittently in the direction of the fluid flow; introducing a solution containing a racemic compound which should be optically separated and an eluent through an inlet port; and simultaneously taking out a solution rich in the weakly adsorbed substances and a solution rich in the strongly adsorbed and desorbed substances through an outlet port.

In the simulated moving bed chromatographic process, a simulated moving bed, which comprises a plurality (12 or 8, for instance) of columns which are serially arranged in the circuit as shown in FIG. 1, is used. The fluid flows only in one direction. The number of the unit columns is not limited to the numbers indicated above but it can be suitably selected depending upon operation scale, consideration on chemical engineering conditions, etc.

In this simulated moving bed, an inlet port for an eluent; an outlet port through which a solution containing an optical isomer easily adsorbable by the filler (extract) is taken out; an inlet port through which a solution containing a racemic compound is introduced; and an outlet port through which a solution containing an optical isomer not easily adsorbed by the filler (raffinate) is taken out are assigned in this order in the direction of fluid flow; and the working positions of these ports are intermittently and successively shifted in the direction of fluid flow.

In a simulated moving bed as shown in FIG. 1, an inlet port for introducing the eluent; an outlet port for taking out the extract; an inlet port for introducing a solution containing a racemic compound; and an outlet port for taking out the raffinate are respectively assigned at every third unit column. In order to intermittently and successively shift the role of the inlet ports and outlet ports, rotary valve, electromagnetic valve, air-actuated valve, etc. are used.

Separation by adsorption of a mevalonolactone compound in the simulated moving bed chromatographic process is basically effected by continuously and cyclically carrying out the adsorption step, the concentration step, the desorption step and the eluent recovery step.

(1) Adsorption Step

A mevalonolactone compound in the form of racemic mixture is made contact with the optical resolution filler, whereby an optical isomer which is strongly adsorbed by the filler (the adsorbable) is adsorbed, and another optical isomer which is not easily adsorbed by the filler (the weakly adsorbable) is recovered together with the eluent.

(2) Concentration Step

The optical resolution filler which has adsorbed the adsorbable is contacted with a portion of the extract described below and the weakly adsorbable which is retained on the optical resolution filler is expelled and thus the adsorbable is concentrated.

(3) Desorption Step

The optical resolution filler which has adsorbed the strongly adsorbable is contacted with the eluent, the adsorbable is expelled from the filler and taken out of the simulating moving bed together with the eluent as extract.

(4) Eluent Recovery Step

The optical resolution filler which contains substantially the eluent only is contacted with a portion of the raffinate and a portion of the eluent contained in the optical resolution filler is recovered as an eluent recovery.

The process is more specifically described with reference to the attached drawing.

In FIG. 1, unit columns 1–12 are filled with an optical resolution filler and they are mutually connected with fluid passages. The eluent is introduced through an eluent supply conduit 13: the extract is taken out through an extract conduit 14, the solution containing a racemic compound is supplied via conduit 15, the raffinate is taken out through a raffinate conduit 16 and the fluid is recirculated through a recirculation conduit 17 by means of a pump 18.

In the state of the unit columns 1–12 and conduits 13–16 as indicated in FIG. 1, desorption is effected in unit columns 1–3, concentration is effected in unit columns 4–6, adsorption is effected in unit columns 7–9 and eluent recovery is effected in unit columns 10–12.

In the simulated moving bed like this, the working positions of the eluent supply conduit, the conduit which supplies a solution containing a racemic compound, respective extract conduits are shifted one unit column by one unit column in the fluid flow direction at a constant time interval by operation of valves.

In the second stage, therefore, desorption is effected in unit columns 2–4, concentration is effected in unit columns 5–7, adsorption is effected in unit columns 8–10 and eluent recovery is effected in unit columns 11–1. By repeating this operation successively, each step is carried out in a set of unit columns which is shifted one column by one column. Thus optical resolution of a mevalonolactone is efficiently achieved.

The extract taken out of the simulated moving bed in accordance with this invention contains an optical isomer at so high purity as not less than 90%, specifically not less than 95% or 98% for instance, and the raffinate contains the other isomer with the same level of the optical purity.

The simulated moving bed to be used for the process of the present invention is not limited to the one shown in FIG. 1 but also the one as indicated in FIG. 2 can be used.

In the arrangement of unit columns 1–8 and conduits 13–16 as shown in FIG. 2, eluent recovery is effected in unit column 1, adsorption is effected in unit columns 2–5, concentration is effected in unit columns 6–7 and desorption is effected in unit column 8 in the first stage.

In this simulated moving bed, the supply conduits and the taking-out conduits are shifted unit column by unit column by valve operation at a constant time interval in the direction of fluid flow. Thus in the next stage, eluent recovery is effected in unit column 2, adsorption is effected in unit columns 3–6, concentration is effected in unit columns 7–8 and desorption is effected in unit column 1.

In FIG. 1, the extract is concentrated in a first falling film evaporator 19, the concentrate is further concentrated in a second falling film evaporator 20, still further in a wiped film evaporator 21; the recovered solvent is stored temporarily in a recovery tank 22, the concentrated solution containing a concentrated optical isomer is stored in a storage tank 23, the raffinate is racemized in a racemization tank 24 and the solvent stored in the recovery tank 22 is concentrated in an evaporator 25.

Meanwhile, the raffinate contains the optical isomer which is an antipode of the isomer contained in the extract. The solvent is recovered from the raffinate in the same manner as recovery of the solvent from the extract.

EMBODIMENTS OF THE INVENTION

Figure 1:
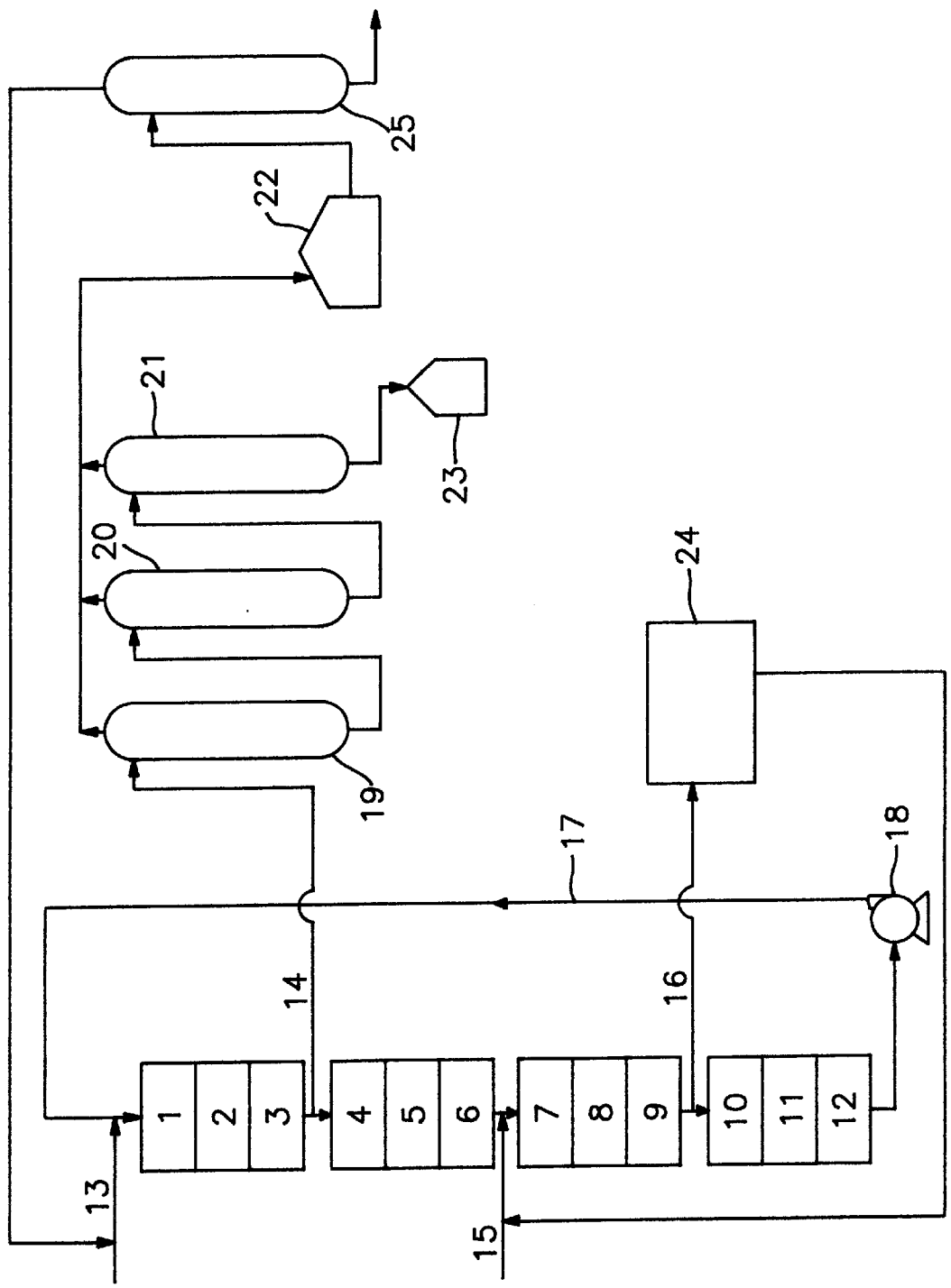
FIG. 1 is the schematic presentation of an apparatus by which the process of the present invention is carried out.
Figure 2:
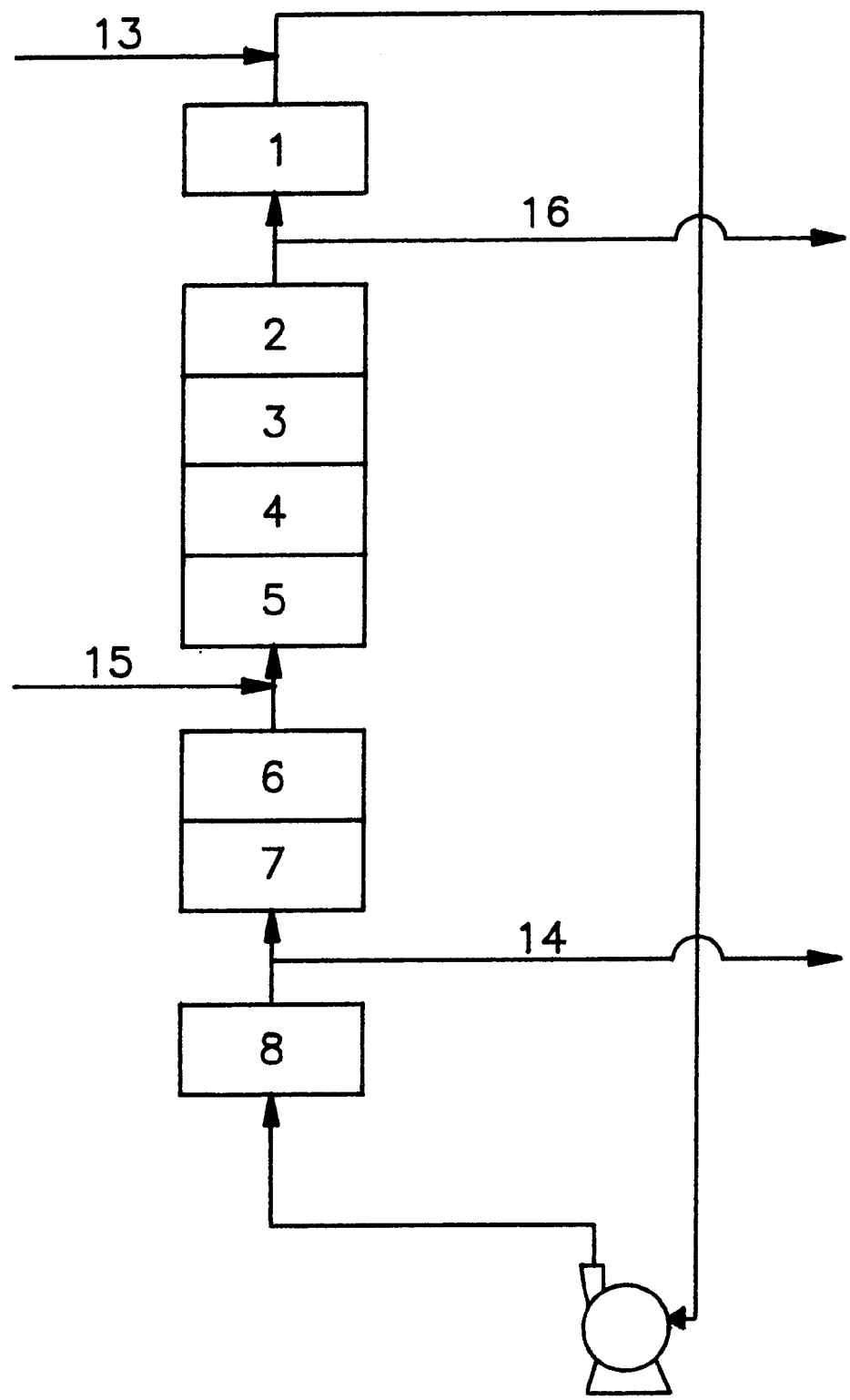
FIG. 2 is the schematic presentation of another apparatus by which the process of the present invention is carried out.

Now the invention is described by way of working examples. Needless to say, the invention is not limited to these examples only but can be worked with suitable modification within the scope of the gist of the invention.

Terms used in the working examples are defined as follows.

Capacity factor k'={(retention time of antipode)−(dead time)}/(dead time)

Separation factor α=(volume ratio of strongly-adsorbed antipode)/(volume ratio of weakly-adsorbed antipode)

Resolution factor Rs=2×(distance between peaks of strongly-adsorbed antipode and weakly-adsorbed antipode)/(sum of bands of two peaks)

EXAMPLE 1

Using a column 0.46 cm in inner diameter and 25 cm in length filled with silica gel supporting cellulose tris(p-chlorophenylcarbamate)("CHIRALCEL OF" marketed by Daicel Chemical Industries, Ltd. ), the (3R,5S) body and the (3S, 5R) body of ethyl 7-[2-cyclopropyl-4-(4-fluorophenyl) quinolin-3-yl]-3,5-dihydroxy-6-heptenoate were optically separated. Conditions of liquid phase chromatography, retention time of the two isomers, capacity factor, separation factor, resolution factor and order of elution are indicated in Table 1.

EXAMPLE 2

Using a column 0.46 cm in inner diameter and 25 cm in length filled with silica gel supporting cellulose tris(p-methylphenylbenzoate) ("CHIRALCEL OJ" marketed by Daicel Chemical Industries, Ltd. ), the (3R,5S) body and the (3S, 5R) body of ethyl 7-[2-cyclopropyl-4-(4-fluorophenyl) quinolin-3-yl]-3,5-dihydroxy-6-heptenoate were optically separated. Conditions of liquid phase chromatography, retention time of the two isomers, capacity factor, separation factor, resolution factor and order of elusion are indicated in Table 1.

EXAMPLE 3

Using a column 0.46 cm in inner diameter and 25 cm in length filled with silica gel supporting cellulose triphenyl-carbamate ("CHIRALCEL OC" marketed by Daicel Chemical Industries, Ltd.), the (3R,5S) body and the (3S, 5R) body of ethyl 7-[2-cyclopropyl-4-(4-fluorophenyl)-quinolin-3-yl] 3,5-dihydroxy-6-heptenoate were optically separated. Conditions of liquid phase chromatography, retention time of the two isomers, capacity factor, separation factor, resolution factor and order of elution are indicated in Table 1.

EXAMPLE 4

Using a column 0.46 cm in inner diameter and 25 cm in length filled with silica gel supporting cellulose tris(3,5-dimethylphenylcarbamate) ("CHIRALCEL OD" marketed by Daicel Chemical Industries, Ltd. ), the (3R,5S) body and the (3S, 5R) body of ethyl 7-[2-cyclopropyl-4-(4-fluorophenyl)-quinolin-3-yl]-3,5-dihydroxy-6-heptenoate were optically separated. Conditions of liquid phase chromatography, retention time of the two isomers, capacity factor, separation factor, resolution factor and order of elution are indicated in Table 1.

EXAMPLE 5

Using a column 0.46 cm in inner diameter and 25 cm in length filled with silica gel supporting cellulose tris(p-methylphenylcarbamate)("CHIRALCEL OG" marketed by Daicel Chemical Industries, Ltd.), the (3R,5S) body and the (3S, 5R) body of ethyl 7-[2-cyclopropyl-4-(4-fluorophenyl) quinolin-3-yl]-3,5-dihydroxy-6-heptenoate were optically separated. Conditions of liquid phase chromatography, retention time of the two isomers, capacity factor, separation factor, resolution factor and order of elution are indicated in Table 1.

EXAMPLE 6

Using a column 0.46 cm in inner diameter and 25 cm in length filled with silica gel supporting amylose tris((s)-1-phenylethylcarbamate) ("CHIRALPAK AS" marketed by Daicel Chemical Industries, Ltd.), racemic ethyl 7-[2-cyclopropyl-4-(4-fluorophenyl)-quinolin-3-yl]-5-hydroxy-3-oxo-6-heptenoate was optically separated. Conditions of liquid phase chromatography, retention time of the two isomers,

TABLE 1

|  | Example 1 | Example 2 | Example 3 | Example 4 | Example 5 |
|---|---|---|---|---|---|
| Filler | CHIRALCEL OF | CHIRALCEL OJ | CHIRALCEL OD | CHIRALCEL OD | CHIRALCEL OG |
| Conditions |  |  |  |  |  |
| Eluent (vol. ratio) | H/I = 80/20 | H/E = 95/5 | H/E = 95/5 | H/I = 95/5 | H/E = 95/5 |
| Flow rate (ml/min.) | 1.0 | 1.0 | 1.0 | 1.0 | 1.0 |
| Column temp. (° C.) | 40 | 22 | 22 | 22 | 22 |
| Detection | UV detector Wave length: 254 nm | | | | |
| Parameters |  |  |  |  |  |
| Retention time (ml/min.) | 10.1<br>13.4 | 37.3<br>43.5 | 37.4<br>40.7 | 23.0<br>25.1 | 34.1<br>37.5 |
| Capacity factor ($k_1'$) | 2.37 | 11.42 | 11.47 | 6.65 | 10.37 |
| Separation factor (a) | 1.47 | 1.18 | 1.10 | 1.11 | 1.11 |
| Resolution factor (Rs) | 3.63 | 1.56 | 0.89 | 1.17 | 1.26 |
| Order of elution | (1) (3R, 5S)<br>(2) (3S, 5R) | (1) (3S, 5R)<br>(2) (3R, 5S) | (1) (3S, 5R)<br>(2) (3R, 5S) | (1) (3R, 5S)<br>(2) (3S, 5R) | (1) (3S, 5R)<br>(2) (3R, 5S) |

TABLE 2

|  | Example 6 | Example 7 |
|---|---|---|
| Filler | CHIRALCEL AS | CHIRALCEL AD |
| Conditions | | |
| Eluent (vol. ratio) | H/I = 90/10 | H/I = 90/10 |
| Flow rate (ml/min.) | 1.0 | 1.0 |
| Column temp. (° C.) | 5 | 40 |
| Detection | UV detector Wave length: 254 nm | |
| Parameters | | |
| Retention time (ml/min.) | 22.5 / 37.7 | 8.2 / 8.9 |
| Capacity factor ($k_1'$) | 6.51 | 1.74 |
| Separation factor (a) | 1.78 | 1.12 |
| Resolution factor (Rs) | 1.56 | 0.51 | capacity factor, separation factor, resolution factor and order of elution are indicated in Table 2.

EXAMPLE 7

Using a column 0.46 cm in inner diameter and 25 cm in length filled with silica gel supporting amylose tris(3,5-dimethylphenylcarbamate) ("CHIRALPAK AD" marketed by Daicel Chemical Industries, Ltd.), racemic ethyl 7-[2-cyclopropyl-4-(4-fluorophenyl)-quinolin-3-yl]-5-hydroxy-3-oxo-6-hepteno-ate were optically separated. Conditions of liquid phase chromatography, retention time of the two isomers, capacity factor, separation factor, resolution factor and order of elution are indicated in Table 2.

EXAMPLE 8

To a simulated moving bed chromatographic apparatus, which comprises eight (8) columns, each having an inner diameter of 1 cm and a length of 25 cm filled with silica gel supporting cellulose tris(p-chlorophenylcarbamate) ("CHIRALCEL OF", particle diameter 20 μm, marketed by Daicel Chemical Industries, Ltd.) racemic ethyl 7-[2-cyclopropyl-4-(4-fluorophenyl)-quinolin-3-yl]-3,5-dihydroxy-6-heptenoate ((3R, 5S) isomer and (3S, 5R) isomer) was supplied at a rate of 1.0 ml/min (racemic mixture concentration 3.5 mg/ml). The apparatus was operated under the following conditions:

Eluent: n-hexane/2-propanol (8/2 vol) mixture

Supply rate of eluent: 7 ml/min

Flow rate at outlet for solution rich in strongly adsorbable: 5.6 ml/min

Flow rate at outlet for solution rich in weakly adsorbable: 2.4 ml/min

Shift interval: 21.0 min

Temperature: room temp.

As a result, out of the outlet port for the fluid rich in the strongly adsorbable, ethyl (−)-7-[2-cyclopropyl-4-(4-fluorophenyl)-quinolin-3-yl]-3,5-dihydroxy-6-heptenoate ((3S,5R) isomer) was obtained with a concentration of 530 ppm and an optical purity of 65% ee. Out of the outlet port for the fluid rich in the weakly adsorbable, ethyl (+)-7-[2-cyclopropyl-4-(4-fluorophenyl)-quinolin-3-yl]-3,5-dihydroxy-6-heptenoate ((3R,5S) isomer) was obtained with a concentration of 894 ppm and an optical purity of 100% ee.

EXAMPLE 9

To a simulated moving bed chromatographic apparatus, which comprises eight (8) columns, each having an inner diameter of 1 cm and a length of 25 cm filled with cellulose tris(p-chlorophenylcarbamate) ("CHIRALCEL OF", particle diameter 20 μm, marketed by Daicel Chemical Industries, Ltd.), communicably connected in series, racemic ethyl 7-[2-cyclopropyl-4-(4-fluorophenyl)-quinolin-3-yl]-3,5-dihydroxy-3,5-dihydroxy-6-heptenoate ((3R, 5S) isomer and (3S, 5R) isomer) was supplied at a rate of 2.0 ml/min (racemic mixture concentration 5.0 mg/ml). The apparatus was operated under the following conditions:

Eluent: n-hexane/2-propanol (8:2 vol) mixture

Supply rate of eluent: 7.2 ml/min

Flow rate at outlet for solution rich in strongly adsorbable: 7.2 ml/min

Flow rate at outlet for the solution rich in the weakly adsorbable: 4.8 ml/min

Shift interval: 9.25 min

Temperature: 25° C.

As a result, out of the outlet port for the fluid rich in the strongly adsorbable, ethyl (−)-7-[2-cyclopropyl-4-(4-fluorophenyl)-quinolin-3-yl]-3,5-dihydroxy-6-heptenoate ((3S,5R) isomer) was obtained with a concentration of 1233 ppm and an optical purity of 45% ee. Out of the outlet for the fluid rich in the weakly adsorbable, ethyl (+)-7-[2-cyclopropyl-4-(4-fluorophenyl)-quinolin-3-yl]-3,5-dihydroxy-6-heptenoate ((3R,5S) isomer) was obtained with a concentration of 1146 ppm and an optical purity of 99% ee.

Industrial Applicability

In accordance with the present invention, mevalonolactone compounds can be efficiently separated and high optical purity mevalonolactone compound can be prepared.

We claim:

1. A process for preparing an optically active mevalonolactone compound comprising conducting optical resolution of the racemic form of an optically active mevalonolactone compound by means of batch system chromatography which uses a column filled with a filler selected from a group consisting of particles of a polysaccharide ester derivative, particles of a polysaccharide carbamate derivative and particles of a support which carries a polysaccharide ester derivative and/or a polysaccharide carbamate derivative.

2. The process for preparing an optically active mevalonolactone compound as described in claim 1, wherein the polysaccharide ester derivative and the polysaccharide carbamate derivative are those in which part of or all of the hydrogen atoms on the hydroxy groups or amino groups of the polysaccharide are substituted with an atom groups represented by any of the following chemical formulas (1) to (4):

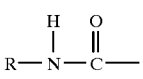

(1)

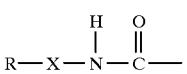

(2)

-continued

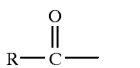
(3)

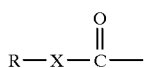
(4)

wherein R stands for an aromatic group which may contain a hetero atom and may be unsubstituted or substituted with at least one selected from a group consisting of an alkyl group having 1–12 carbon atoms, an alkoxy group having 1–12 carbon atoms, an alkylthio group having 1–12 carbon atoms, a cyano group, a halogen atom, an acyl group having 1–8 carbon atoms, an acyloxy group having 1–8 carbon atoms, a hydroxy group, an alkoxycarbonyl group having 1–12 carbon atoms, a nitro group, an amino group and an alkylamino group having 1–8 carbon atoms; and X stands for a hydrocarbon group having 1–4 carbon atoms, which may contain a double bond or triple bond.

3. A process for preparing an optically active mevalonolactone compound comprising forming a circulation flow circuit comprising a plurality of columns filled with an optical resolution filler and endlessly connected in series; enforcing a fluid to flow through the circuit in one direction; providing each with an inlet port through which the fluid is introduced into the column in the flow direction and with an outlet port, through which the fluid is taken out; intermittently shifting the working position of the inlet port and a suitably-spaced outlet port in the direction of the fluid flow; introducing a solution containing a racemic mevalonolactone compound and an eluent through an inlet port into the circuit; and simultaneously taking out a solution rich in the weakly adsorbable and a solution rich in the strongly adsorbable through the outlet port, wherein the optical resolution filler is one selected from a group consisting of particles of a polysaccharide ester derivative, particles of a polysaccharide carbamate derivative and particles of a support which carries a polysaccharide ester derivative and/or a polysaccharide carbamate derivative.

4. The process for preparing an optically active mevalonolacton compounds as described in claim 3, wherein the polysaccharide ester derivative and the polysaccharide are those in which part of or all of the hydrogen atoms on the hydroxy groups or amino groups of the polysaccharide are substituted with any of the atom groups represented by the following chemical formulas (1) to (4):

(1)

H O
| ||
R—N—C—

(2)

H O
| ||
R—X—N—C—

(3)

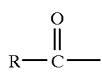

(4)

wherein R stands for an aromatic group which may contain a hetero atom and may be unsubstituted or substituted with at least one selected from a group consisting of an alkyl group having 1–12 carbon atoms, an alkoxy group having 1–12 carbon atoms, an alkylthio group having 1–12 carbon atoms, a cyano group, a halogen atom, an acyl group having 1–8 carbon atoms, an acyloxy group having 1–8 carbon atoms, a hydroxy group, an alkoxycarbonyl group having 1–12 carbon atoms, a nitro group, an amino group and an alkylamino group having 1–8 carbon atoms; and X stands for a hydrocarbon group having 1–4 carbon atoms, which may contain a double bond or triple bond.

5. The process for preparing an optically active mevalonolactone compound as described in any of claims 1 to 4, wherein the optically active mevalonolacton compound is ethyl 7-[2-cyclopropyl-4-(4-fluorophenyl)quinolin-3-yl]-5-hydroxy3-oxo-6-heptenoate or ethyl 7-[2-cyclopropyl-4-(4-fluorophenyl)quinolin-3-yl]-3,5-dihydroxy-6-heptenoate.

* * * * *